(12) United States Patent
Krosney

(10) Patent No.: US 11,406,729 B2
(45) Date of Patent: Aug. 9, 2022

(54) AIR TREATMENT SYSTEM AND METHOD

(71) Applicant: EDHM Holdings, LLC, Fort Pierce, FL (US)

(72) Inventor: Mark D. Krosney, Port St. Lucie, FL (US)

(73) Assignee: AEROCLEAN TECHNOLOGIES, LLC, Palm Beach Gardens, FL (US)

( * ) Notice: Subject to any disclaimer, the term of this patent is extended or adjusted under 35 U.S.C. 154(b) by 139 days.

(21) Appl. No.: 16/640,192

(22) PCT Filed: Mar. 25, 2018

(86) PCT No.: PCT/US2018/024228
§ 371 (c)(1),
(2) Date: Feb. 19, 2020

(87) PCT Pub. No.: WO2019/045777
PCT Pub. Date: Mar. 7, 2019

(65) Prior Publication Data
US 2020/0376152 A1    Dec. 3, 2020

Related U.S. Application Data

(60) Provisional application No. 62/552,547, filed on Aug. 31, 2017.

(51) Int. Cl.
*A61L 9/20* (2006.01)
*B01D 46/00* (2022.01)
(Continued)

(52) U.S. Cl.
CPC ............... *A61L 9/20* (2013.01); *B01D 46/10* (2013.01); *B01D 50/00* (2013.01); *B01J 19/08* (2013.01);
(Continued)

(58) Field of Classification Search
CPC ............ A61L 9/20; B01J 19/08; B01D 46/10; B01D 50/00
See application file for complete search history.

(56) References Cited

U.S. PATENT DOCUMENTS

| 5,225,167 A | 7/1993 | Wetzel |
| 5,505,904 A | 4/1996 | Haidinger et al. |

(Continued)

FOREIGN PATENT DOCUMENTS

| CN | 101639267 A | 2/2010 |
| CN | 202198889 U | 4/2012 |

(Continued)

OTHER PUBLICATIONS

International Search Report and the Written Opinion of the International Searching Authority received from the Korean Intellectual Property Office in International Application No. PCT/US2018/024228 dated Jul. 13, 2018.

(Continued)

*Primary Examiner* — Robert A Hopkins
(74) *Attorney, Agent, or Firm* — The Marbury Law Group, PLLC

(57) ABSTRACT

Systems and methods for reducing airborne contaminants are provided. An air treatment system may include an opening and a filter assembly, a fan coupled to a sanitizing chamber, and an exhaust portion configured to release airflow that has passed through the sanitizing chamber. The fan may be configured to generate an airflow of filtered air through the sanitizing chamber, and the sanitizing chamber may include at least one bend having a total bend angle of at least 90 degrees and at least one straight channel with an array of ultraviolet (UV) light emitting diodes (LEDs) configured to irradiate the airflow with UV radiation. A ratio (Continued)

of a total length of the sanitizing chamber to a cross-sectional area of the sanitizing chamber may be at least 25.

16 Claims, 14 Drawing Sheets

(51) Int. Cl.
  *B01D 50/00* (2022.01)
  *B01J 19/08* (2006.01)
  *B01D 46/10* (2006.01)

(52) U.S. Cl.
  CPC ....... *A61L 2209/14* (2013.01); *B01D 46/0036* (2013.01); *B01D 2259/804* (2013.01); *B01D 2273/30* (2013.01)

(56) References Cited

U.S. PATENT DOCUMENTS

| | | | |
|---|---|---|---|
| 5,626,820 | A | 5/1997 | Kinkead et al. |
| 5,689,364 | A | 11/1997 | McGregor et al. |
| 5,761,908 | A | 6/1998 | Oas et al. |
| 5,964,792 | A | 10/1999 | Augustine |
| 6,039,926 | A | 3/2000 | Goldman |
| 6,053,968 | A | 4/2000 | Miller |
| 6,254,337 | B1 | 7/2001 | Arnold |
| 6,322,614 | B1 | 11/2001 | Tillmans |
| 6,464,760 | B1 | 10/2002 | Sham et al. |
| 6,541,777 | B1 | 4/2003 | Lombardo et al. |
| 6,797,044 | B2 | 9/2004 | Ou Yang et al. |
| 6,893,610 | B1 | 5/2005 | Barnes |
| 6,949,223 | B2 | 9/2005 | McEllen |
| 7,175,814 | B2 | 2/2007 | Dionisio |
| 7,498,004 | B2 | 3/2009 | Saccomanno |
| 8,236,236 | B2 * | 8/2012 | Garner ................ B01D 53/32 422/3 |
| 8,980,178 | B2 | 3/2015 | Gaska et al. |
| 2003/0170151 | A1 | 9/2003 | Hunter et al. |
| 2005/0000365 | A1 | 1/2005 | Nelsen et al. |
| 2005/0163648 | A1 | 7/2005 | Liang |
| 2005/0173352 | A1 | 8/2005 | Burrows et al. |
| 2005/0242013 | A1 | 11/2005 | Hunter et al. |
| 2006/0159594 | A1 | 7/2006 | Parker et al. |
| 2007/0102280 | A1 * | 5/2007 | Hunter ................ A61L 9/16 204/157.15 |
| 2007/0196235 | A1 | 8/2007 | Shur et al. |
| 2008/0095661 | A1 | 4/2008 | Kohler |
| 2009/0004047 | A1 | 1/2009 | Hunter et al. |
| 2009/0041632 | A1 | 2/2009 | Day et al. |
| 2009/0084734 | A1 | 4/2009 | Yencho |
| 2009/0098014 | A1 | 4/2009 | Longstaff |
| 2009/0252646 | A1 | 10/2009 | Holden et al. |
| 2010/0132715 | A1 | 6/2010 | Litz |
| 2010/0143205 | A1 | 6/2010 | Engelhard |
| 2010/0260644 | A1 | 10/2010 | Day et al. |
| 2010/0279595 | A1 | 11/2010 | Horstman et al. |
| 2011/0033346 | A1 | 2/2011 | Bohlen et al. |
| 2012/0118150 | A1 | 5/2012 | Brizes et al. |
| 2012/0168641 | A1 | 7/2012 | Lizotte |
| 2012/0273340 | A1 | 11/2012 | Felix |
| 2012/0285459 | A1 | 11/2012 | Sata et al. |
| 2013/0238042 | A1 | 9/2013 | Gildersleeve et al. |
| 2013/0313104 | A1 | 11/2013 | Yates |
| 2014/0017135 | A1 | 1/2014 | Boodaghians et al. |
| 2014/0030144 | A1 | 1/2014 | Krosney et al. |
| 2014/0271374 | A1 | 9/2014 | Giles et al. |
| 2014/0348701 | A1 | 11/2014 | Kirschman |
| 2016/0038624 | A1 | 2/2016 | Krosney |
| 2017/0000916 | A1 | 1/2017 | Stibich et al. |
| 2017/0296690 | A1 | 10/2017 | Matsui et al. |
| 2017/0307234 | A1 | 10/2017 | Matschke et al. |
| 2019/0084852 | A1 | 3/2019 | Harris |
| 2019/0160190 | A1 | 5/2019 | Kreitenberg |
| 2020/0108166 | A1 | 4/2020 | Rhoden |
| 2020/0144601 | A1 | 5/2020 | Takahashi et al. |
| 2020/0230267 | A1 | 7/2020 | Greenfield |

FOREIGN PATENT DOCUMENTS

| | | |
|---|---|---|
| CN | 203980947 | 12/2014 |
| CN | 205181843 | 4/2016 |
| CN | 111093822 | 5/2020 |
| EP | 2 554 583 A1 | 2/2013 |
| EP | 2 921 183 A1 | 9/2015 |
| JP | H06-12773 U | 2/1994 |
| JP | 2000-008178 A | 1/2000 |
| JP | 2000-070928 A | 3/2000 |
| JP | 2001-224672 A | 8/2001 |
| JP | 2001-293072 A | 10/2001 |
| JP | 2001-520552 A | 10/2001 |
| JP | 2003-088571 A | 3/2003 |
| JP | 2004-504869 A | 2/2004 |
| JP | 2005-166180 A | 6/2005 |
| JP | 2005-203437 A | 7/2005 |
| JP | 2005-253799 A | 9/2005 |
| JP | 2007-511279 A | 5/2007 |
| JP | 2008-259809 A | 10/2008 |
| JP | 2009-22903 A | 2/2009 |
| JP | 2009-181914 A | 8/2009 |
| JP | 2009-532200 A | 9/2009 |
| JP | 2011-530542 A | 12/2011 |
| JP | 2012-512723 A | 6/2012 |
| KR | 200315033 | 5/2003 |
| KR | 1020190000715 | 1/2019 |
| WO | 98/47545 A2 | 10/1998 |
| WO | 02/04036 A1 | 1/2002 |
| WO | 2005/011753 A1 | 2/2005 |
| WO | 2007113537 A1 | 10/2007 |
| WO | 2010071814 A1 | 6/2010 |
| WO | 2011087100 A1 | 7/2011 |
| WO | 2015/131243 A1 | 9/2015 |
| WO | 2016081703 A1 | 5/2016 |
| WO | 2017070359 A1 | 4/2017 |
| WO | 2020151918 | 7/2020 |

OTHER PUBLICATIONS

International Preliminary Report on Patentability received from the Korean Intellectual Property Office in International Application No. PCT/US2018/024228 dated Dec. 16, 2019.
Extended European Search Report received in related European Patent Application No. 18851780.9-1104 / 3675919 PCT/US2018/024228 dated May 27, 2021.
Decision of Refusal received in related Japanese Patent Application No. 2018-540690 dated Jul. 1, 2021.
International Preliminary Report on Patentability and Written Opinion of the International Searching Authority in related International Application No. PCT/US2021/033752 dated Sep. 16, 2021.
Extended European Search Report from the European Patent Office in Application No. 14829593.4-1370 / 3024503 in International Application No. PCT/US2014/048144 dated Feb. 2, 2017.
International Search Report and the Written Opinion of the International Searching Authority in International Application No. PCT/US2016/057932 dated Feb. 3, 2017.
International Preliminary Report on Patentability received from the Korean Intellectual Property Office in related International Application No. PCT/US2018/024229 dated Dec. 19, 2019.
First Examination Report (FER) received from the Indian Patent Office in related Indian Patent Application No. 201637004406 dated Oct. 25, 2020.
Extended European Search Report received from the The Hague Patent Office in related European Application No. EP 16 85 8222 dated May 22, 2019 PCT/US2016/057932.
European Communication Pursuant to Rules 70(2) and 70a(2) EPC from the European Patent Office in related European Application No. EP 16 85 8222 dated Jun. 7, 2019 PCT/US2016/057932.
International Search Report and the Written Opinion of the International Searching Authority received from the Korean Intellectual Property Office in PCT Application No. PCT/US2018/024229 dated Jul. 13, 2018.

(56) References Cited

OTHER PUBLICATIONS

International Search Report and Written Opinion of the International Searching Authority for International Application No. PCT/US2018/024229 dated Jul. 13, 2018. 12 pages.
International Preliminary Report on Patentability received from the Korean Intellectual Property Office in International Application No. PCT/US2016/057932 dated Feb. 1, 2018.
1st Examination Report received from the Saudi Patent Office in Saudi Arabia Patent Application No. 516370810 dated Nov. 13, 2017.
First Notification of Reasons for Refusal received from the Japanese Patent Office in related Japanese Patent Application No. 2016-530064 dated May 31, 2018.
Notification of Reasons for Refusal cited in related Patent Application No. JP 2018-540690 dated Sep. 3, 2020.
Written Opinion of the International Preliminary Examination Authority cited in related Patent Application No. PCT/US2018/024229 dated Oct. 24, 2019.
1st Office Action received from the EPO in related European Patent Application No. EP 14829593.4 dated Nov. 6, 2020.
Japan Patent Office, Notice of Reasons for Refusal in Japanese Patent Application No. JP 2020-534160, including English-language translation, dated Jan. 3, 2022, (7 pages).
Korean Intellectual Property Office, International Search Report and Written Opinion in corresponding International Application No. PCT/US2021/050342 dated Dec. 31, 2021 (10 pages).
Japanese Patent Office, Reconsideration Report by Examiner before Appeal in related Japanese Patent Application No. 2018-540690 dated May 9, 2022.

\* cited by examiner

0° Bend

L/A Ratio = 0.89

L/A Ratio = 4

AIR TREATMENT SYSTEM AND METHOD

RELATED APPLICATIONS

This is a national stage application of PCT/US2018/024228, filed on Mar. 25, 2018, which claims priority to U.S. Provisional Application No. 62/552,547, filed on Aug. 31, 2017, both of which are incorporated by reference herein in their entireties.

BACKGROUND

The role of air quality in personal health is increasingly recognized as important to preventing illness due to airborne contaminants. Fine particulates make their way into individuals' lung tissues, adversely impacting their respiratory systems. Additionally, certain pathogens may be transmitted in aerosolized droplets from an infected person. These aerosolized droplets may stay in a room for a long period of time after the infected person has vacated the room. Breathing in such aerosolized droplets may infect a new person. Further, the amount of such pathogen required to cause infection through airborne transmission is often far less than through direct contact.

Recently, there has been a growing number systems and devices designed to reduce airborne pathogens in hospital and home settings in order to lower infection rates. Such devices may treat room air using ultraviolet ("UV") or high-efficiency particulate air ("HEPA") type filtering, or a combination thereof. Further, there is an interest in employing the air treatment devices used in hospitals in other settings (e.g., residential, work, travel, etc.), for example, to combat common and seasonal outbreaks of infections. However, in order to provide adequate airflow and a very high pathogen kill rate, such devices are typically large in size and may be impractical for home use.

For example, the typical configuration of such commercial and hospital devices often require difficult maintenance for the average user. In particular, filter replacement is often a difficult process and may further expose a user attempting to replace filters to the pathogens. Further, UV devices are typically expensive, and may have the potential to expose users to escaped UV radiation. Moreover, to achieve the air flow required to effectively treat the air within a typical room, a fan may be employed. Such fans tend to generate a significant amount of noise that becomes a nuisance in non-hospital settings. Therefore, while UV air treatment implemented in air purification/treatment devices may be useful in residential settings, various issues relating to effectiveness, design, and safety hinder their widespread application.

BRIEF DESCRIPTION OF THE DRAWINGS

The accompanying drawings, which are incorporated herein and constitute part of this specification, illustrate exemplary aspects of the invention. Together with the general description given above and the detailed description given below, the drawings serve to explain features of the invention.

DETAILED DESCRIPTION

Figure 1:
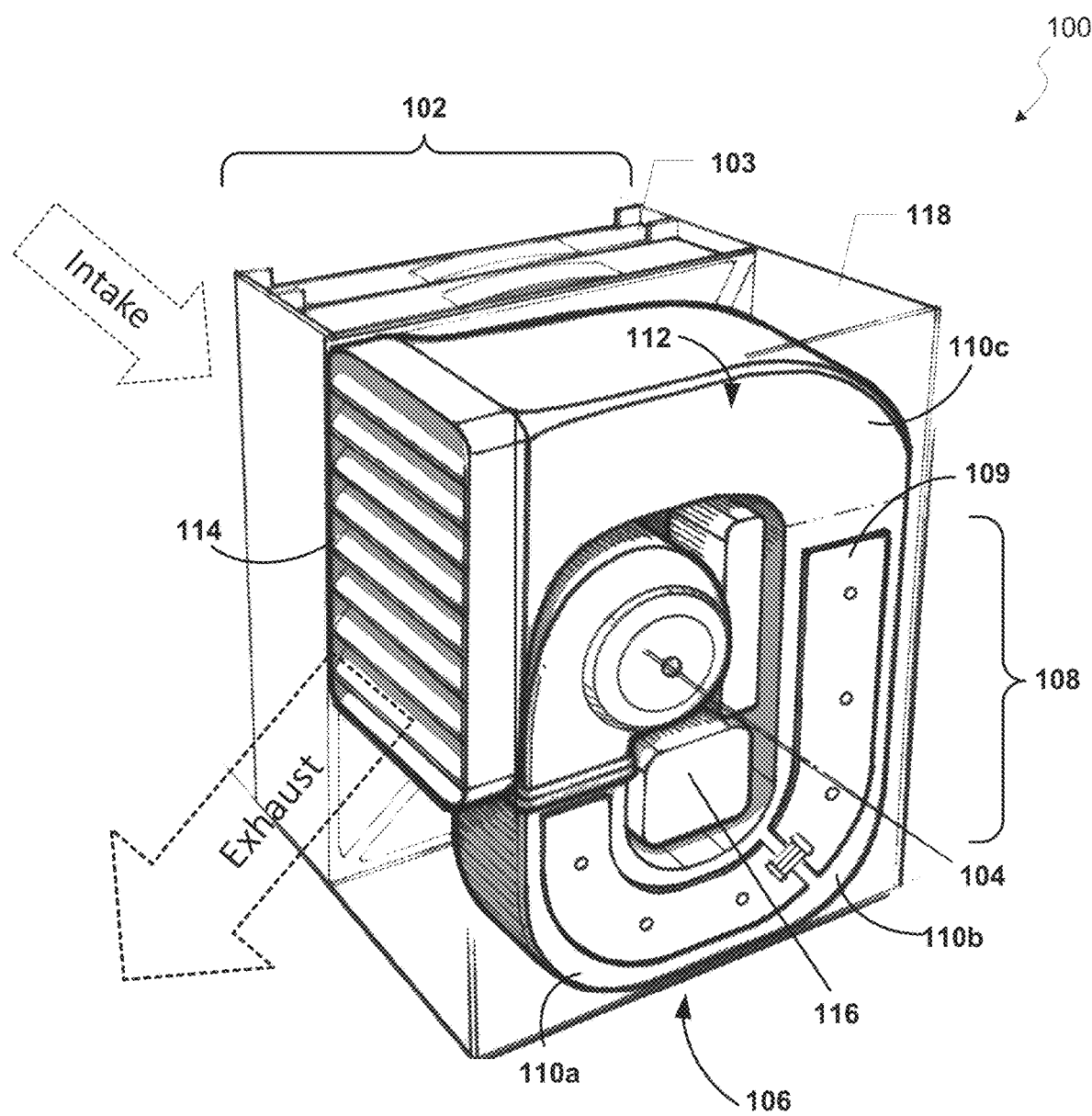
FIG. 1 is a cutaway view of an air treatment device according to various embodiments.

The various embodiments will be described in detail with reference to the accompanying drawings. Wherever possible, the same reference numbers will be used throughout the drawings to refer to the same or like parts. References made to particular examples and implementations are for illustrative purposes and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

The term "UV radiation" is used herein to mean high energy UV-C photons with wavelengths shorter than 290 nm, which are capable of traversing cellular walls. In various embodiments, the UV radiation utilized for air treatment may be at one or multiple wavelengths within the range of 200 to 320 nm range.

The terms "flux" and "radiation flux" are used herein to mean the amount of radiation at the specified wavelength that reaches the surface of airborne pathogens. The terms "dwell time" and "residence time" are used herein to refer to the duration of time that the airborne pathogens remain exposed to the radiation flux.

The terms "contaminants" is used herein to refer to impurities, including all of biological agents (e.g., pathogens), chemical agents, pollutant particles, volatile organic compounds, and chemical vapors.

Systems and devices in various embodiments provide an effective, safe, and convenient method for substantially eliminating airborne pathogens within a room. In various embodiments, an air treatment system may be compact and quiet to provide optimal performance for use in a residential environment.

In various embodiments, an air treatment system may employ one or more filter to capture contaminants dispersed in the air as well as UV radiation emitted within a sanitizing chamber that is configured to optimize performance while killing at least 95% of airborne pathogens. In various embodiments, the UV radiation may be emitted by one or more array of light emitting diodes (LEDs). The air treatment system may include an intake area with an opening to the surrounding air, and a filter assembly. Air that passes through the opening may be filtered by the filter assembly, and through the system for purification. A fan may transport the filtered air from the intake area to a sanitizing chamber, which may be connected to an exhaust portion that releases treated air back into the surrounding environment. In some embodiments, control circuitry may be included within the air treatment system to regulate power supplied to the UV LEDs and fan. The various components of the air treatment system may be enclosed within a compact housing.

In various embodiments, the sanitizing chamber may include at least one straight channel and at least one bend, forming a shape that is configured to prevent spurious UV radiation from escaping the sanitizing chamber while providing the airflow with sufficient UV radiation dosage to achieve a desired kill rate (e.g., at least 95%).

In various embodiments, at least one array of high-output UV-emitting LEDs may be positioned within at least one straight section of the sanitizing chamber. The UV LEDs are selected based upon the desired wavelength and power rating. In some embodiments, the UV LEDs in the at least one array emit radiation at one or more wavelength within the range of 240-280 nm, such as within the range of 260-270 nm.

The internal surface of one or more section of the sanitizing chamber may be coated with a reflective material. In some embodiments, the internal surface of the sanitizing chamber may be configured with a band of UV radiation-absorptive material at the edges adjacent to the fan and the exhaust portion in order to mitigate potential UV radiation escape. In some embodiments, any other surface that is exposed by line of sight to both the exhaust portion and the reflective material may also be coated with a UV radiation-absorptive material.

Design of the air treatment system for residential use may include minimizing noise production from the fan. Therefore, the fan included in embodiment air treatment systems may be of the smallest size and/or operate at a minimum level needed to provide an effective flow rate to mobilize latent pathogens within the room for treatment. For example, such effective flow rate may be within the range of 180 to 300 cubic feet per minute, such as 250 cubic feet per minute. In various embodiments, the configuration of the sanitizing chamber is critical in order to manage the UV radiation flux and effectively sanitize the room air without compromising the desired airflow rate. Generally, increasing the length of the pathway as well as the number and degree of bends of an airflow pathway leads to longer residence time for the airflow, and therefore improves effectiveness of the UV radiation in killing airborne pathogens. However, such increases lengthen to the path of the airflow, also increases the pressure drop over the system. Increases in pressure drops over the systems may result in an increase in overall noise generated by the system. Thus, designs of such systems seek to mitigate such pressure drops. Also, a high level of reflectance within the sanitizing chamber generally maximizes the effectiveness of the UV LEDs. However, in certain settings (e.g., residential), ensuring that such reflected radiation does not escape the sanitizing chamber is critical. As a result, the fan output required to achieve the same flow rate would be increased. In systems for residential use, the level of noise generated by operation of an air treatment system directly depends on the fan requirements, and should be minimized for user comfort.

These constraints may be balanced to provide a compact, low noise, air treatment device that achieves a sufficient pathogen kill rate for home use, yet prevents users from exposure to the UV radiation in the system. Specifically, a ratio of a radius of curvature of the at least one bend to a length of a sterilization region in the sanitizing chamber may be configured to minimize pressure drop across the air treatment system, while enabling at least a 95% reduction of airborne pathogens from the airflow and substantially no escape of UV radiation.

In some embodiments, the filter assembly and diffusion region may be configured to reduce pressure drop in the system. For example, the pre-filter and one or more filter may have a maximum surface area enabled by the system design, thereby minimizing resistance through the filter assembly. Further, the diffusion region may have a graduated shape that widens toward the exhaust portion, thereby shortening the flow path of air before it is released. In some embodiments, an exhaust portion may connect to a diffusion region of the sanitizing chamber configured to prevent escape of UV radiation. In various embodiments, a cross-sectional area of the diffusion region in the sanitizing chamber may be graduated such that the largest area is adjacent the exhaust portion. The diffusion region may also include one or more bend, which may have a smaller radius of curvature than the other bend(s) in the sanitizing chamber. In some embodiments, the one or more bend in the diffusion region may be in a different plane than the other bend(s) in the sanitizing chamber.

In various embodiments, the filter assembly may include a pre-filter that captures large particulate materials from the intake airflow. The filter assembly may include a HEPA filter to capture and remove fine particles from the airflow, such as after exposure to the pre-filter. In some embodiments, the HEPA filter may have a minimum efficiency of 99.97% arrestance at 0.3 micrometers, as set forth by standards of the U.S. Department of Energy. In some embodiments, the filter assembly may additionally or alternatively include a carbon-activated filter to remove gaseous pollutants from the airflow, for example, after passing through a pre-filter and/or the HEPA filter.

In various embodiments, an electronics and control module may regulate power input into an air treatment device, driving the fan and UV LEDs. The electronics and control module may operate with conventionally available power supplies and contain a circuit breaker.

FIG. 1 illustrates a residential air treatment device 100 according to various embodiments. The device 100 may include an intake area 102, which may include an opening to allow air into the device, and a filter assembly 103for removing particles and contaminants in the air. In various embodiments, the filter design may have a maximum surface area relative to the overall size of the device 100 to contribute to a reduction in pressure drop. For example, the filter assembly 103 may be configured to fit within a housing panel that is about 12 inches long by 24 inches tall. The filtered air may feed into a fan 104 that generates airflow through a sanitizing chamber 106. The sanitizing chamber 106 may have at least one sterilization region 108, and at least one bend 110a-110c. The sterilization region 108 in some embodiments may be a straight channel that includes a UV LED array 109.

The straight channel 108 may be configured with a sufficient length to expose air within the sanitizing chamber 106 to a predetermined UV radiation dosage for sterilization.

In various embodiments, the intake of filtered air into the fan 104 may flow in a plane that is perpendicular to the path of the airflow through the sanitizing chamber, including in the bends 110a-110c. The number, curvature, and position of the bends 110a-110c in the sanitizing chamber 106 may be optimized to reduce the pressure drop in the system while preventing escape of substantially all UV radiation and exposing the airflow to a sufficiently high UV radiation dosage. The UV LEDs of the array may be positioned to obtain the maximum amount of UV reflectance based on the configuration of the straight channel 108 and the bends 110a-110c, as well as to avoid escape of the UV radiation from the sanitizing chamber 106. In various embodiments, such positioning may be obtained using ray tracing technology.

The interior surface of the bends 110a, 110b, and/or the straight channel 108, in the sanitizing chamber may be coated with a highly reflective material, such as polished aluminum. In some embodiments, the interior surface of the bends 110a, 110b and/or the straight channel 108 may be coated with a naturally germicidal material, such as copper or copper alloy.

The sanitizing chamber 106 may also include a diffusion region 112, which may have a shape that widens as the distance from the UV LED array(s) increases, thereby reducing pressure drop. The diffusion region 112 may also have a bend to prevent escape of UV radiation from the sanitizing chamber 106. In various embodiments, the bend of the diffusion region 112 may have a different curvature radius than the bends 110a-110c. For example, where the diffusion region 112 has a wider area for the airflow than the rest of the sanitizing chamber 106, the curvature radius of the bend in the diffusion region 112 may be smaller than that of one or more bend 110a-110c. That is, the diffuser region 112 is configured with a tighter bend in order to minimize the escape of UV radiation out of the wider area. In some embodiments, the diffusion region 112 may also be coated with a UV radiation-absorptive material.

The diffusion region 112 may be coupled to an exhaust portion 114 to expel treated airflow from the device 100. In some embodiments, the bend of the diffusion region 112 may be in the same plane as one or more bend 110a-110c. In other embodiments, the bend of the diffusion region 112 may be in a different plane than the one or more bend 110a-110c, such as a plane that is perpendicular to the airflow path through the rest of the sanitizing chamber 106.

In some embodiments, the airflow of the air treatment device 100 may be within the range of about 100 cubic feet per minute (cfm) to about 700 cfm. In some embodiments, the air treatment device 100 may be configured such that the pressure drop is within the operating parameters of the fan 104. For example, if the fan 104 is capable of producing an airflow of 500 cfm, the total pressure drop may be less than 0.7 inches of water. In some embodiments, the airflow within the sanitizing chamber may have one or more areas of turbulence within the sanitizing chamber, providing a high Reynolds number (e.g., Reynolds number above 20,000).

An electronics and control module 116 may be incorporated to regulate power supplied to the at least one array of UV LEDs and to the fan 104. The electronics and control module 116 may be provided as one or multiple units/integrated circuits, and may be coupled to a power supply for the air treatment device 100. In various embodiments, the air treatment device 100 may include any number of additional components, all of which may be enclosed within a compact housing 118.

As described, while the sanitizing chamber is configured to expose the airflow to a sufficiently high UV radiation dosage, a number of parameters of the sanitizing chamber may be adjusted to optimally prevent escape of the UV radiation, while maintaining a compact size and low noise production of the device. In particular, such parameters may include those affecting the geometry of the sanitizing chamber, such as the total bend angle for the airflow in the sanitizing chamber, and the ratio of the sanitizing chamber length to its diameter. The diameter of the sanitizing chamber in various embodiments may be represented by its cross-sectional area ("L/A ratio"), which may be calculated by multiplying the width of the sanitizing chamber by its height.

In some embodiments, the total bend angle may be the result of one bend, such as between a straight channel 108 and the diffusion region 112 may (e.g., bend 110c). In some embodiments, the total bend angle may be the result of a plurality of bends in the sanitizing chamber 108 (e.g., bends 110a-110c). For example, the sanitizing chamber may have between two and five bends, which may be in one or multiple orientation planes.

In various embodiments, the sanitizing chamber may have dimensions such that the L/A ratio is at least 25, and may be configured with a total bend angle of at least 90 degrees, such as 90-180 degrees. Within these ranges, such parameters may be adjusted to comport with the specific features, measurements, and other properties of the device, as well as minimize size and pressure drop (i.e., noise).

This analysis considers two variations of geometry; the angle between input and output, and the ratio of cross sectional area to length. FIG. 2A illustrates an example configuration of the parts that make up the intake area of an embodiment air treatment device 200. The intake area 202 of the device 200 may include a pull-away panel 204 that allows a user to easily access the filter assembly 103 to install and/or replace various filters. The pull-away panel 204 may provide an opening through which room air passes into the device 200 through the filter assembly.

The filter assembly 103 may include a pre-filter 206 directly adjacent the pull-away panel 204 in the intake area, and at least one filter 208 directly adjacent the pre-filter 206. The pre-filter 206 may eliminate any large particulate matter that is suspended in the room air. The at least one filter 208 may be, for example, a filter that is configured to remove fine particulate matter from airflow (e.g., activated carbon filter, HEPA filter, etc.).

A user may engage the pull-away panel 204 to clean or replace one or more part of the filter assembly, thereby exposing the user to the fan and sanitizing chamber. As such, the sanitizing chamber in the various embodiments may be configured to prevent escape of UV radiation, thereby preventing exposing to a user if the pull-away panel 204 and/or filter assembly are removed.

Figure 2B:
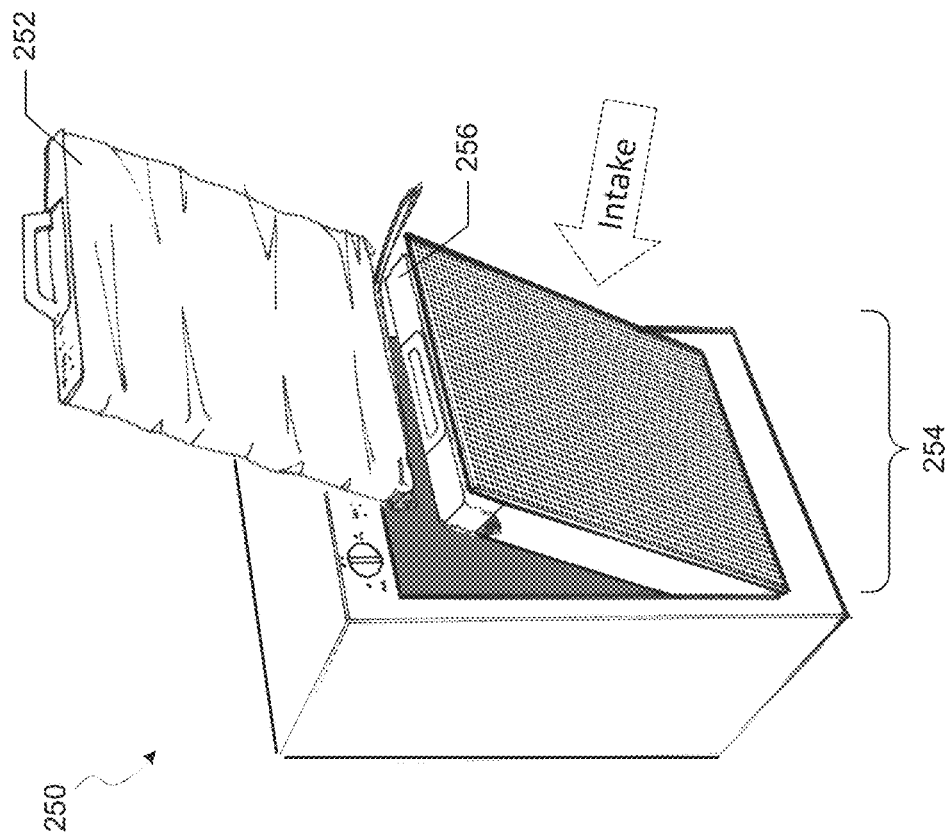
FIGS. 2A and 2B are elevation views of an air treatment device according to various embodiments.
Figure 2A:
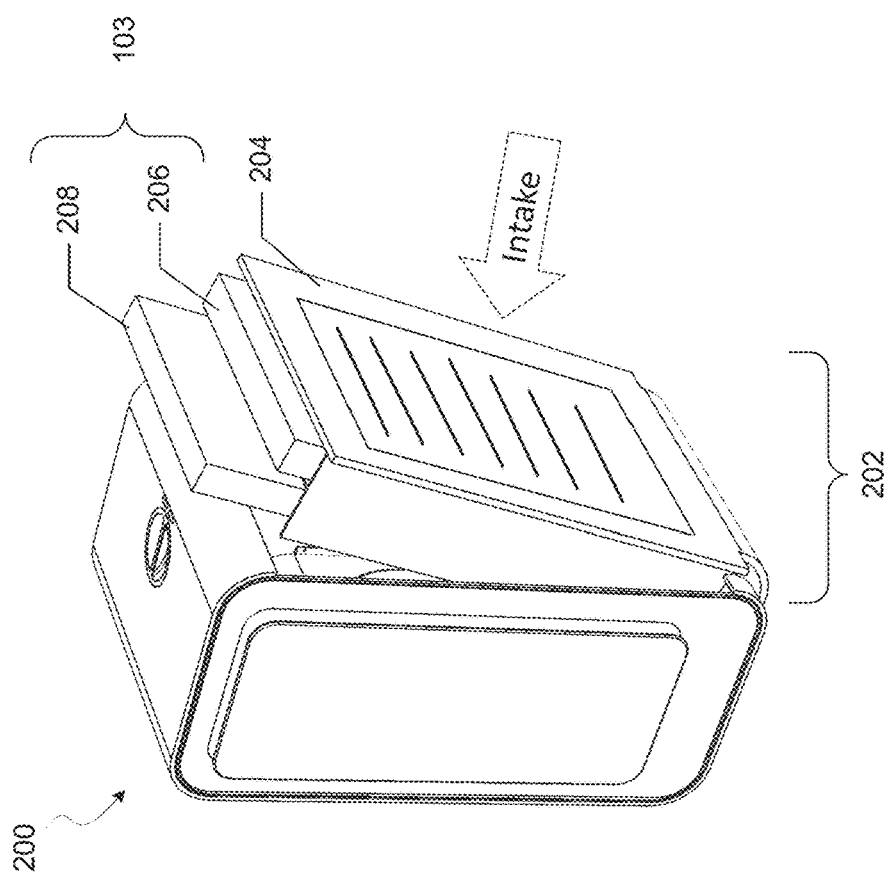

FIG. 2B illustrates another example configuration of the parts that make up the intake area of an embodiment air treatment device 250. With reference to FIG. 2A, the filter assembly may include a bag deployed over the at least one filter (e.g., 206, 208) for easier cleaning and replacement. In various embodiments, a bagged filter unit 252 may be configured with tabs to properly attach the unit 252 within the intake area 254, behind the pre-filter 256. Upon installation, tabs may allow the bagged filter unit 252 to slide into place behind a pre-filter (e.g., 204) and compress the bag. When it is determined that the filter assembly should be replaced, the bagged filter unit 252 may slide out of the intake area 254, which allows the bag to redeploy and trap dust and debris. In some embodiments, a sleeve (not shown) may be permanently or removably attached to the air treatment device 250 in the intake area 254. The sleeve may be positioned near the top of the intake area 254, and may slide down to extend over a filter that is installed behind the pre-filter 256. When the filter is removed, the sleeve may retract back to its original position near the top of the intake area 254.

In some embodiments, each filter (e.g., 206, 208) and/or filter assembly (e.g., 103, 252) may be configured with a specific identifier within an automatic identification and data capture (AIDC) system. Such identifier may be provided on an electronic label, for example, on a radio frequency identification (RFID) tag, a magnetic stripe, etc. A corresponding reader for the electronic label may be provided in the portion of the intake area that receives the filter (e.g., 206, 208) or filter assembly (e.g., 103, 252), enabling identification of the unique filter or filter assembly upon installation. The control unit may be configured to store the identifier of the installed filter or filter assembly in associated memory (e.g., RAM), or in a separate storage device (e.g., hard disk, CD-ROM, flash drive, etc.), which may be coupled to the control unit. Thereafter, when the filter or filter assembly needs to be replaced, the air treatment device may cease operation if the user attempts to reuse an old filter or filter assembly. Such measure may promote proper maintenance of the air treatment device, thereby ensuring the level of performance for which it was designed.

Figure 3A:
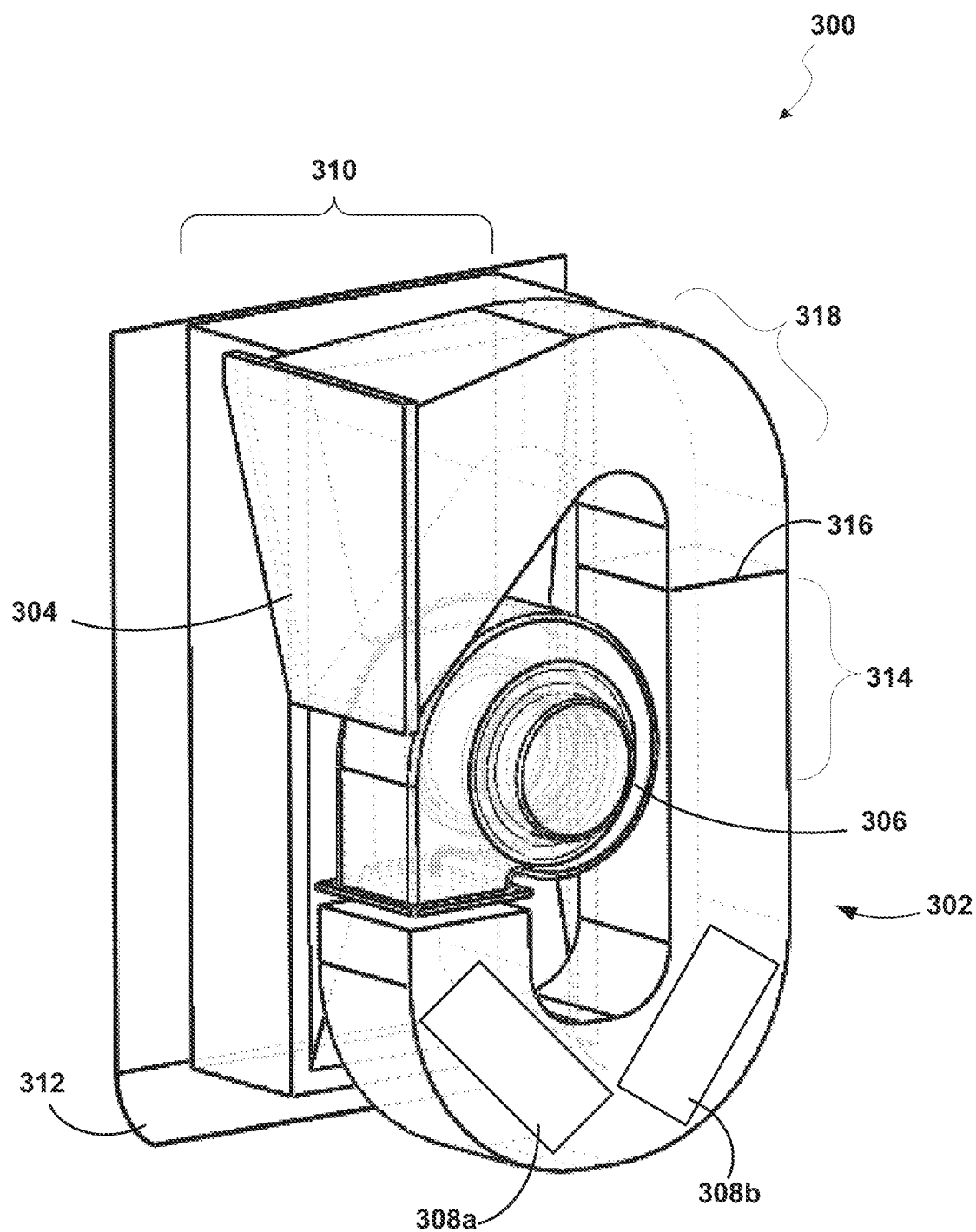
FIG. 3A is a cutaway view of an embodiment pre-packaged set suitable for use in an air treatment device.

In some embodiments, the size of various components of airflow treatment systems may be designed to provide convenient packaging and/or assembly. For example, FIG. 3A illustrates a pre-packaged set 300 that includes a sanitizing chamber 302, exhaust portion 304, fan 306, UV LED arrays 308a, 308b, and intake area 310 that enable a seller or user to easily assemble an airflow treatment device. The components of the prepackaged set 300 may be optimized for residential use as described above, within the size constraints of a housing panel 312 included with the prepackaged set. In some embodiments, the interior surface of a first portion 314 of the sanitizing chamber 302 (e.g., below line 316) may be made of or coated with a material that reflects UV radiation. The interior surface of a second portion 318 of the sanitizing chamber 302 (e.g., above line 316) and of the exhaust portion 304 may be made of or coated with a material that absorbs UV radiation.

Figure 3B:
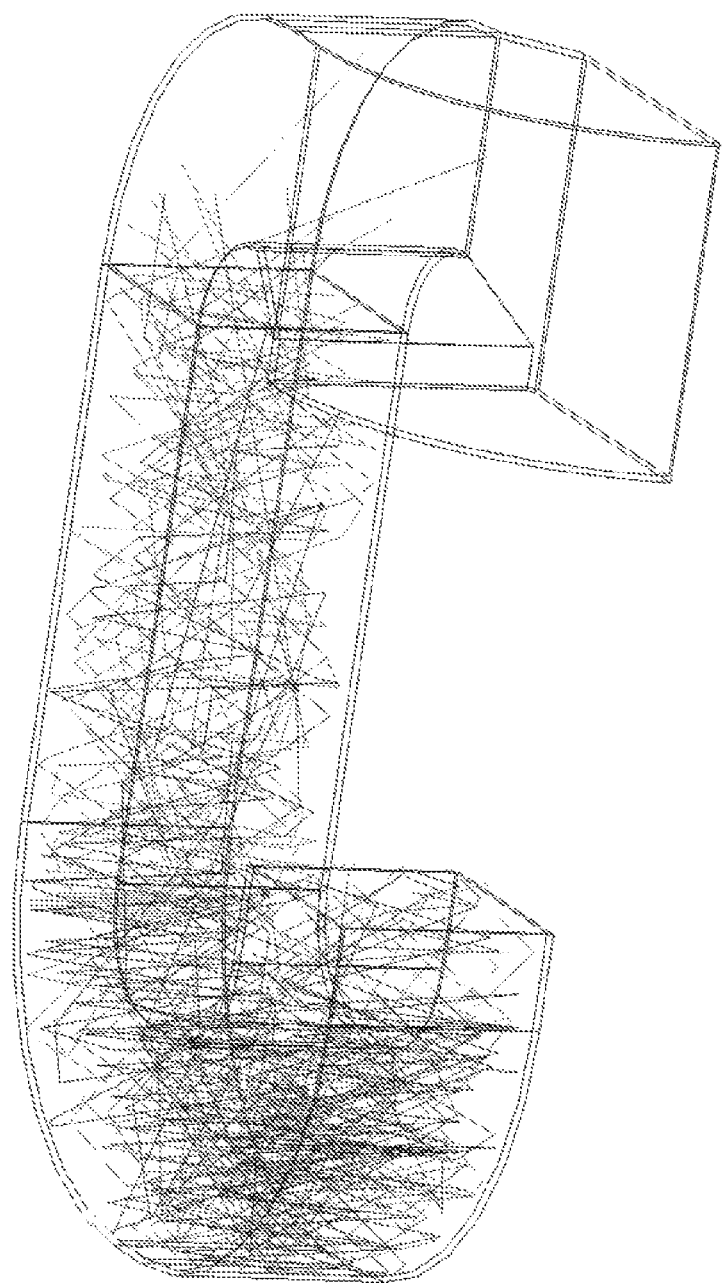
FIG. 3B is a computer-generated three-dimensional representation of the reflectance of UV radiation within the sanitizing chamber of the air treatment device of FIG. 3A.

As described, UV LED arrays may be positioned to obtain the maximum amount of UV reflectance based on the configuration of the straight channel and bends in the sanitizing chamber, as well as to avoid escape of the UV radiation. FIG. 3B illustrates the results of UV radiation reflectance tracing technology applied to the sanitizing chamber 302 and exhaust portion 304 of the pre-packaged set 300 in FIG. 3A. In various embodiments, such ray tracing may be used to calculate the optimum position for the UV LED arrays given the pre-packaged set measurements.

Figure 4:
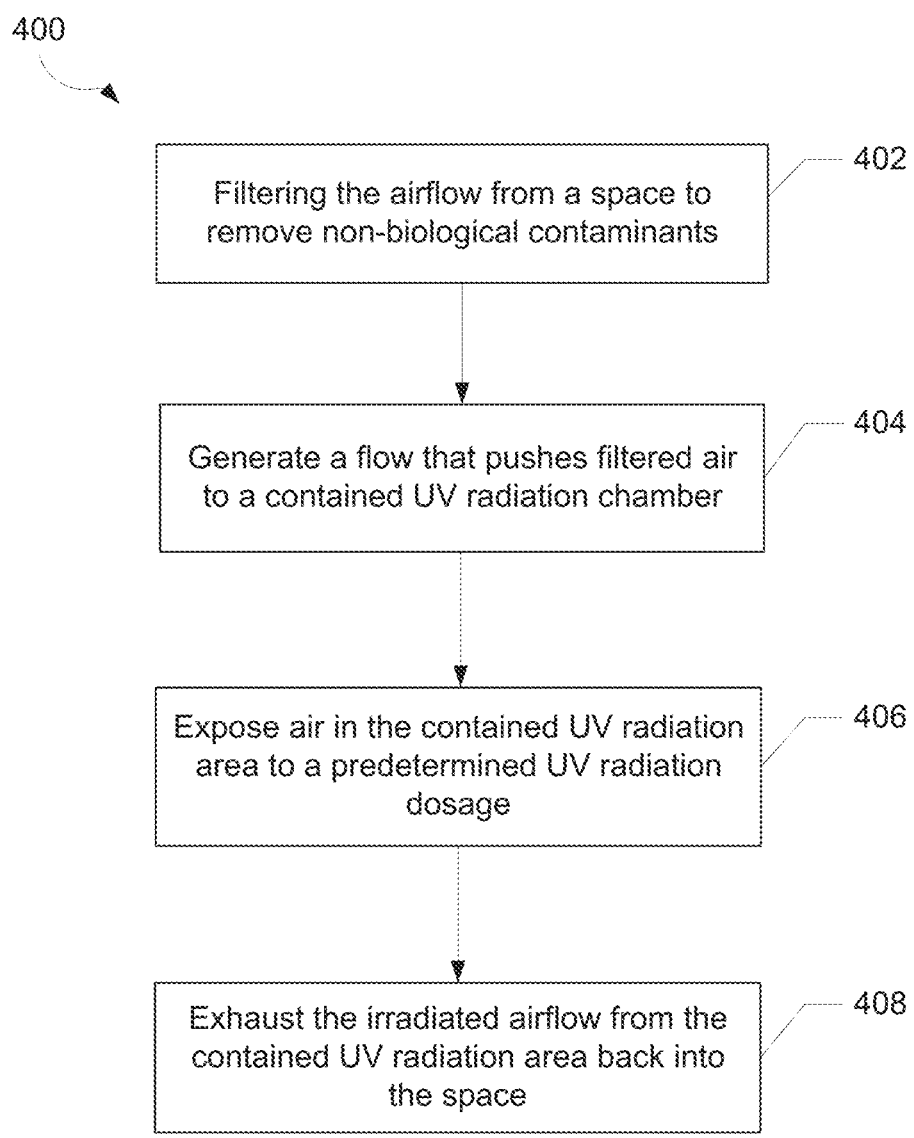
FIG. 4 is a process flow diagram illustrating a method for reducing airborne contaminants in a space according to various embodiments.

FIG. 4 shows an embodiment method 400 for reducing airborne contaminants within a room. In block 402, airflow from a space may be filtered to remove non-biological contaminants. For example, such filtering may involve using a pre-filter for large particulates, and/or at least one filter that removes fine particulates (e.g., HEPA filter) and/or that adsorbs harmful gasses (e.g., volatile organic chemical filter). In block 404, a flow may be generated that pushes the filtered air into a contained UV radiation area. In various embodiments, the airflow may be generated by a fan, and the contained UV radiation exposure area may be a chamber with an array of UV LEDs. In various embodiments, the shape and size of the contained UV radiation area, and the position of the UV LEDs, may be configured to prevent spurious UV radiation outside of the contained area.

In block 406, the air in the contained UV radiation area may be exposed to a predetermined UV radiation dosage. Such predetermined UV radiation dosage may be achieved by optimizing the number and position of the UV LEDs and the materials used within the contained UV radiation area interior, and configuring the contained UV radiation area to allow for a necessary residence time. In various embodiments, the predetermined UV radiation dosage for a residential room may be sufficient to kill or disable at least 95% of airborne pathogens within the airflow.

In block 408, the irradiated airflow may be exhausted from the contained UV radiation area back into the room.

In some embodiments, additional functionality may be added to an air treatment system by including specialized components. For example, a UV sensor may be disposed within the sanitization chamber of embodiment air treatment devices in order to monitor the radiation flux and ensure proper operation. In various embodiments, such UV sensor may use one or more UV photodetector, such as those based on gallium nitride (GaN), indium gallium nitride (InGaN), and/or aluminum gallium nitride (AlGaN) materials. In various embodiments, the UV sensor may be configured to communicate with an externally visible indicator to confirm to the user that the device is working. In some embodiments, the indicator may be included as part of an air treatment device, whereas in other embodiments the indicator may be provided by a separate device in wireless communication with the air treatment device.

Figure 5:
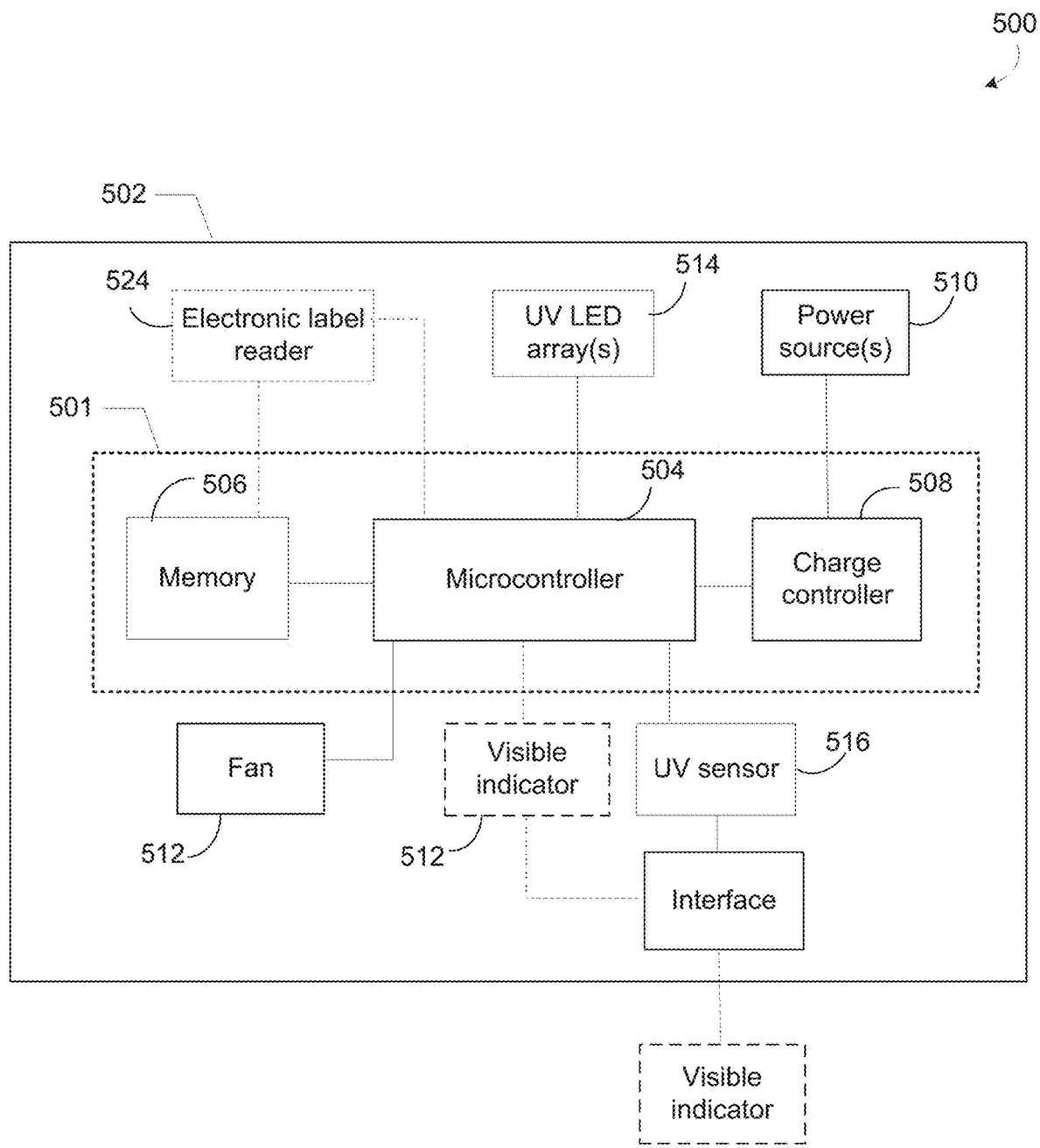
FIG. 5 is a component block diagram of an air treatment system according to various embodiments.

FIG. 5 illustrates components of an example air treatment system 500. In system 500, an electronics and control module 501 may be implemented on a circuit board within an air treatment device 502. The electronics and control module 502 may include a microcontroller 504 coupled to a memory device 506 and a charge controller 508. The charge controller 508 may connect to at least one power source 510, which may be an AC power supply and/or a battery. Other components within the air treatment system 500 may include a fan 512, one or more UV LED array 514, and a UV sensor 516. The UV sensor 516 may be connected to an interface 518 that connects one or more visible indicator. An optional visible indicator 520 may be provided as part of the air treatment device 502. The visible indicator 520 may be coupled to the microcontroller 504 and the interface 518. Another optional visible indicator 522 may be provided as an external component, which may be part of another device or system (e.g., a smartphone, tablet, etc.). The interface 518 may connect the visible indicator 522 through a wireless communication link.

The device 502 may optionally include an electronic label reader 524 (e.g., RFID reader) coupled to the microcontroller 504 and the memory 506. As discussed above, the RFID reader 524 may be configured to receive an identifier when a new filter assembly is installed, and compare the received identifier to any that have been previously stored. If the new identifier matches a previously-stored identifier, operation of the device 502 may be deactivated. Otherwise, the received identifier may be stored in the memory 506.

In various embodiments, the electronics and control module may be mounted to the housing outside of the sanitizing chamber. The UV LEDs of the one or more array may be electrically connected to the electronics and control module and fixedly attached to mated openings in the walls of a portion of the sanitizing chamber (e.g., straight channel) such that the UV LED array circuit boards are outside of the sanitizing chamber and the UV LEDs irradiate inside the sterilization region of the sanitizing chamber. The UV sensor may be electrically connected to the electronics and control module and fixedly attached to a mated opening in the wall of the sterilization region of the sanitizing chamber such that the sensor can detect irradiance levels.

EXAMPLES

The effects of two different variations in the sanitizing chamber were tested for efficacy in preventing UV radiation escape. The sanitizing chamber that was used had an overall length of 36 inches, and was equipped with four Nikkiso VPS131 producing 10 mW of radiation at 265 nm.

A coating of Alanod MIRO2 (4200GP) was applied to create the reflective surface within the reflective portion of the sanitizing chamber, resulting in a reflectivity of 95%, The surface within the diffuser portion of the sanitizing chamber was hard coat anodized, resulting in an absorptivity of 90%. Results were assessed in the context of the exposure limit to UV radiation based on a maximum daily exposure of 30 J/m$^2$, set forth in "A Non-Binding Guide to the Artificial Optical Radiation Directive 2006/25/EC, by the European Agency for Safety and Health at Work. Specifically, the exposure limit for a duration of 8 hours is provided at 1 mW/m$^2$.

Ray tracing analysis was used to provide the average power of UV radiation leakage at the exhaust end of the sanitizing chamber.

Example 1: Angle of Bend in Sanitizing Chamber

Sanitizing chambers were created with two 18 inch sections connected by a single bend, which has an angle of either 90 degrees or 180 degrees. A comparative sanitizing chamber having a bend angle of 0 degrees (i.e., no bend) was also created. The sanitizing chambers each had a fixed cross-sectional area of 18.06 in$^2$ (i.e., 4.25 inches wide by 4.25 inches high). The average irradiance leakage from the sanitizing chambers having these bend angles was measured, with the following results:

| Bend Angle | Average UV radiation leakage (mW/m$^2$) | Percentage of maximum leakage | Percent reduction from maximum average |
|---|---|---|---|
| 0° | 4.69 | 100.00% | 0% |
| 90° | 0.288 | 6.14% | −93.86% |
| 180° | 0.125 | 2.67% | −97.33% |

The results above indicate that the use of a straight (i.e., 0° of bend) sanitizing chamber with a 2.0 L/A ratio does not attenuate the irradiance leakage, resulting in an average UV radiation leakage that is above the 1 mW/m$^2$ Artificial Optical Radiation Directive 8 hour exposure limit.

Figure 6A:
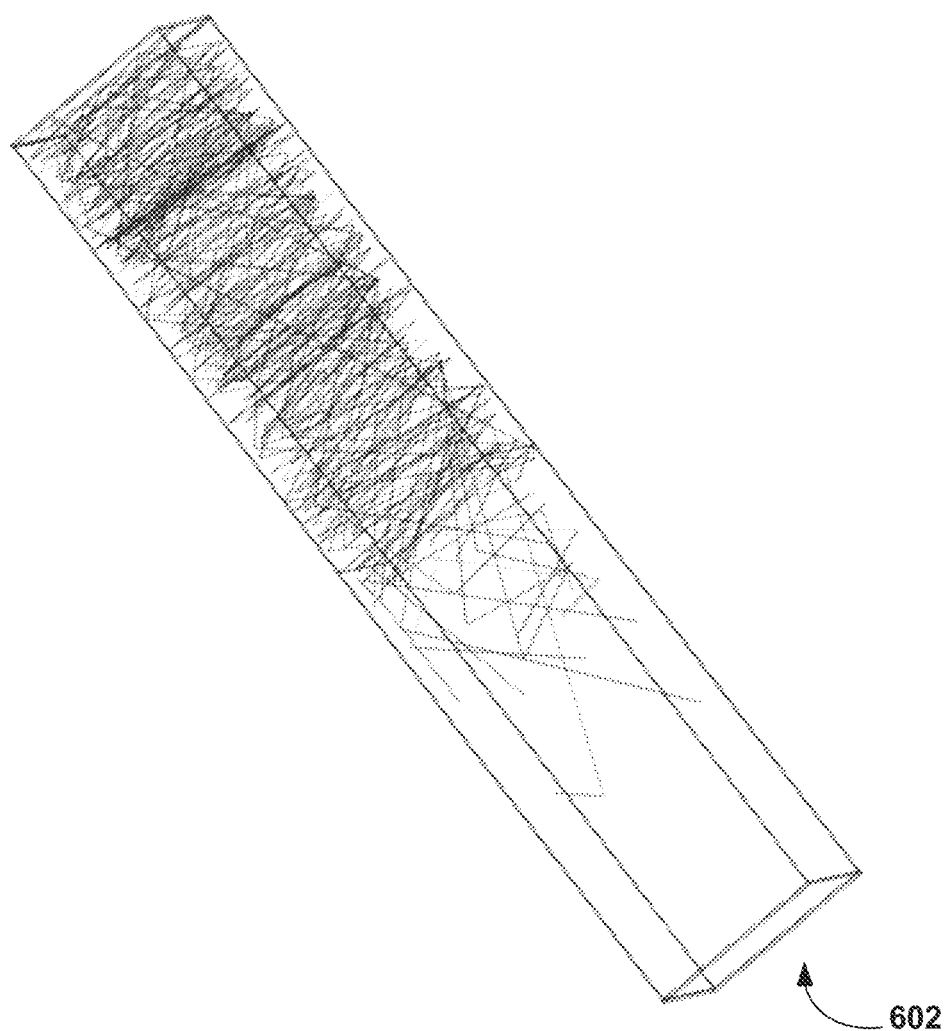
FIGS. 6A-6C are computer-generated three-dimensional representations of the reflectance of UV radiation within straight sanitizing chambers having various bend angles.
Figure 6B:
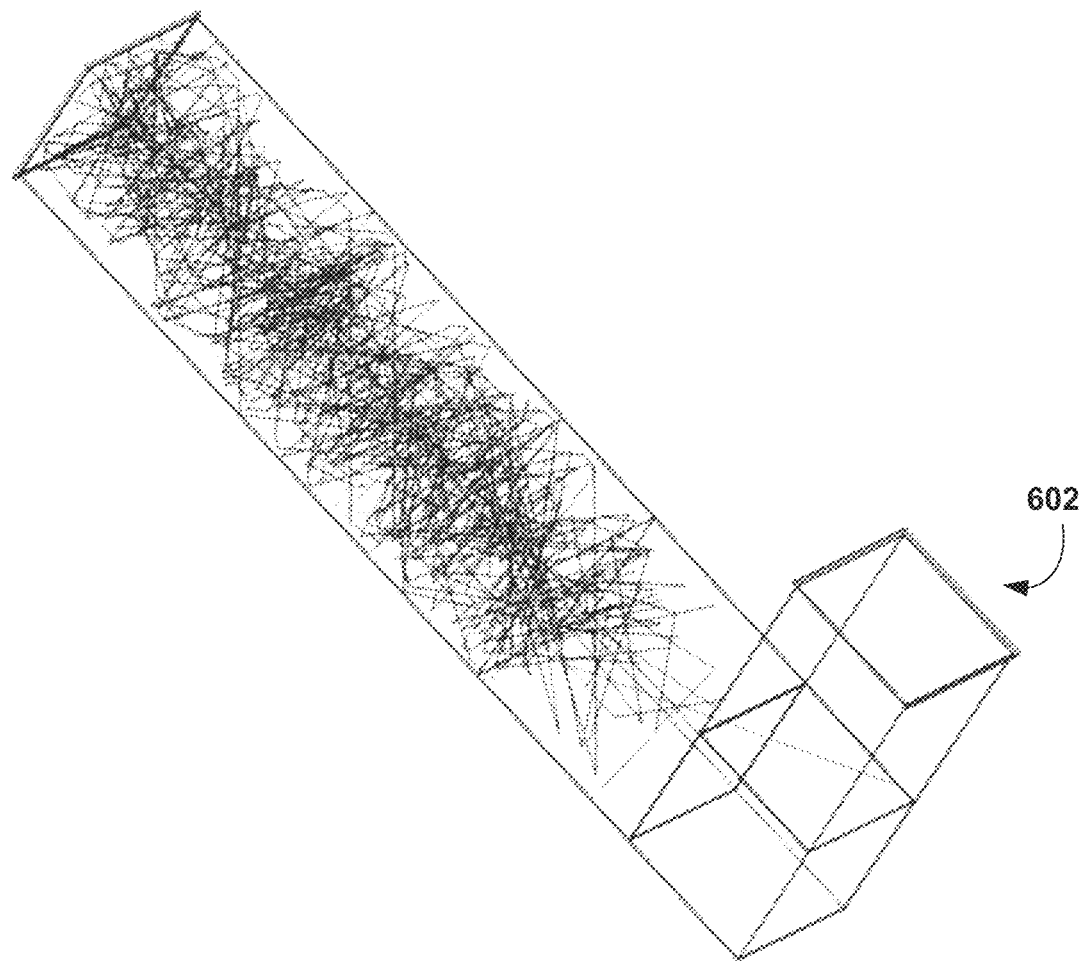
Figure 6C:
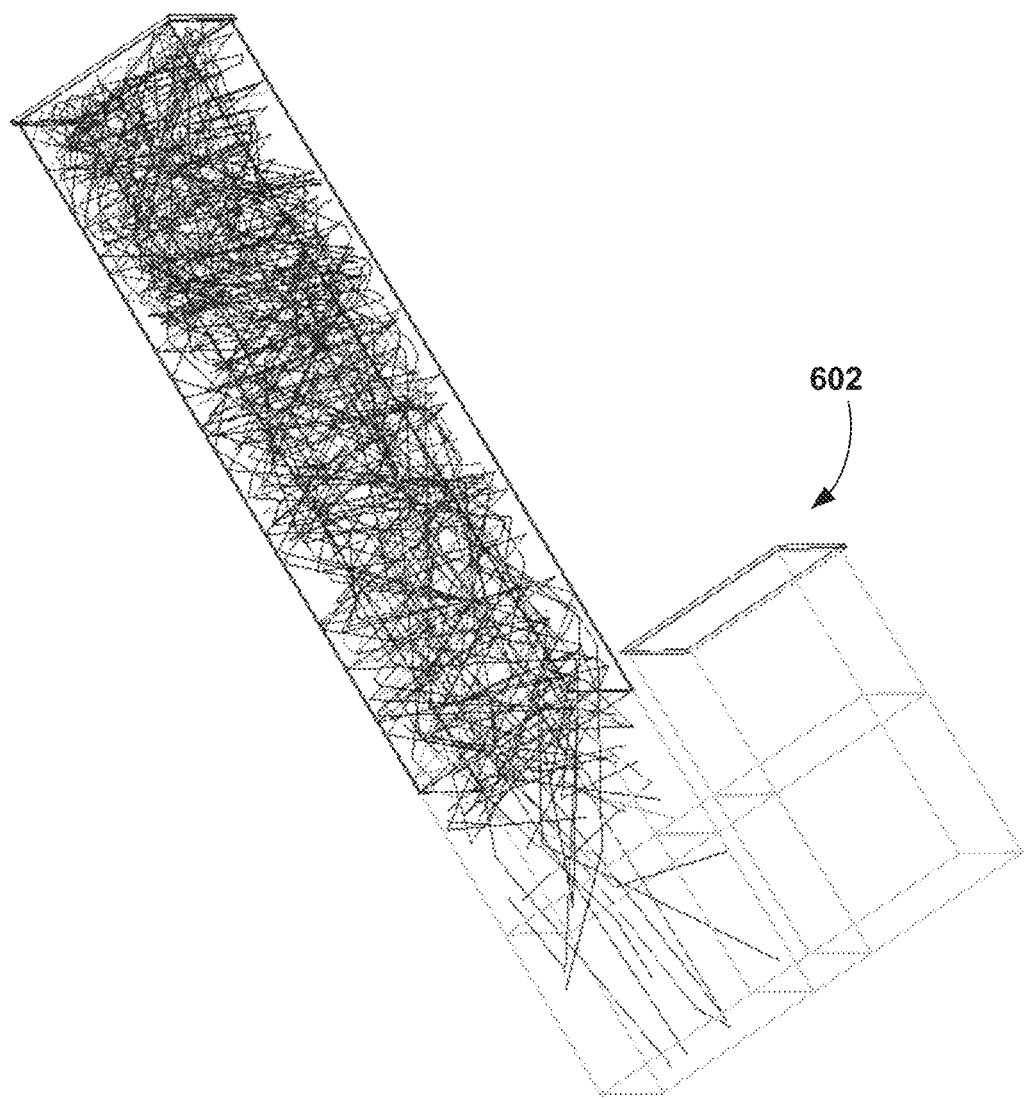
Figure 6F:
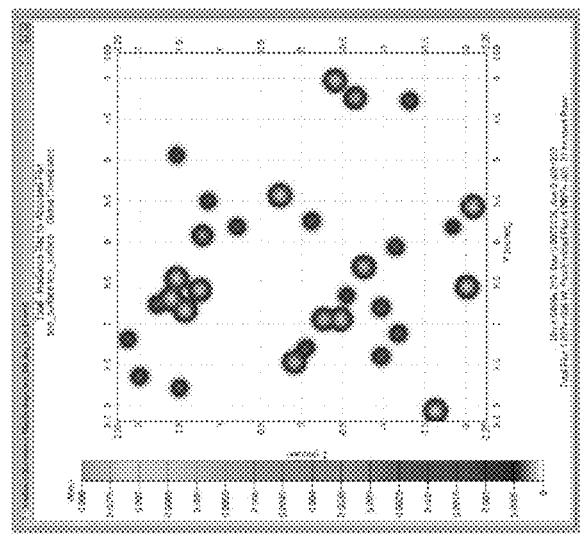
FIGS. 6D-6F are computer-generated irradiation maps showing the amount of incident UV radiation escape from the sanitizing chambers represented in FIGS. 6A-6C, respectively.
Figure 6E:
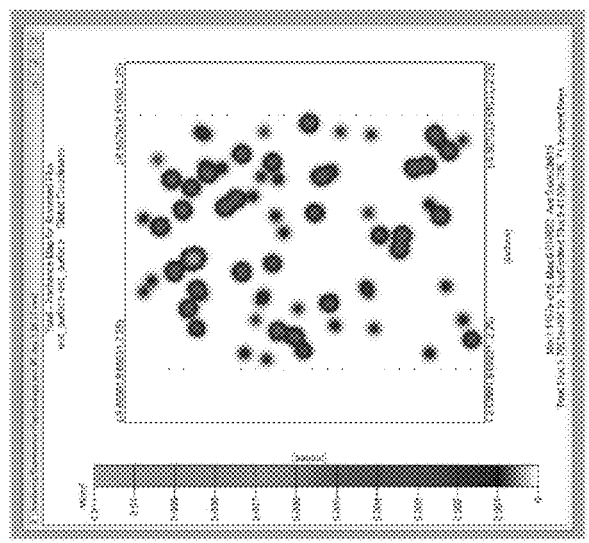
Figure 6D:
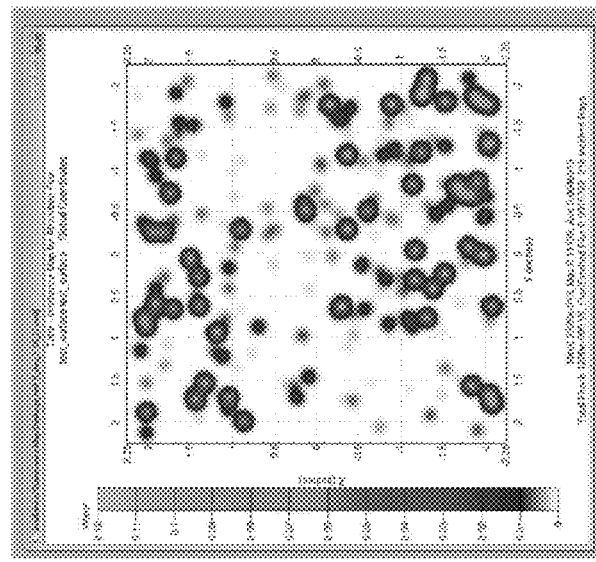

The results above indicate that the bend angles of 90 degrees and 180 degrees reduce the UV radiation leakage by 93.86% and 97.33% respectively, over the 0 degrees/maximum leakage baseline, and provide average irradiation measurements that are well under the 1 mW/$m^2$ limit Computer-generated models tracing the reflectance of UV radiation rays in three-dimensional space within each of the tested sanitizing chambers (i.e., with 0°, 90°, and 180° of bend) are shown in FIGS. 6A-6C, respectively. FIGS. 6D-6F are irradiation maps that show the amount of incident UV radiation escaping the respective sanitizing chambers modeled in FIGS. 6A-6C. Specifically, the irradiation maps in FIGS. 6D-6F each provide the computer-modeled density of UV radiation rays measured at a cross-section near the exit end 602 of the particular sanitizing chamber.

A visual comparison of FIGS. 6D-6F demonstrates that the lowest level of UV radiation escape occurs in FIG. 6F, which corresponds to the model of the sanitizing chamber having 180° of bend, shown in FIG. 6C.

Example 2: Length to Cross-Sectional Area Ratio of Sanitizing Chamber

Ten sanitizing chambers having a length of 36 inches were created with varying width and height dimensions, listed below:

| No. | Width (in) | Height (in) | Cross-sectional area (in$^2$) |
|---|---|---|---|
| 1 | 1.00 | 1.00 | 1.00 |
| 2 | 1.20 | 1.20 | 1.44 |
| 3 | 1.50 | 1.50 | 2.25 |
| 4 | 2.19 | 2.19 | 4.80 |
| 5 | 2.68 | 2.68 | 7.20 |
| 6 | 3.00 | 3.00 | 9.00 |
| 7 | 3.21 | 3.21 | 10.29 |
| 8 | 4.25 | 4.24 | 18.02 |
| 9 | 6.375 | 6.375 | 40.64 |
| 10 | 8.5 | 8.5 | 72.25 |

Based on their dimensions, the L/A ratios of the sanitizing chambers 1-10 ranged from 0.5 to 36. The sanitizing chambers each had a fixed bend angle of 0 degrees (i.e., no bend). The average irradiance leakage from each of sanitizing chambers 1-10 was measured, for which results are provided below with the corresponding L/A ratio:

| No. | L/A ratio | Average UV radiation leakage (mW/m$^2$) | Cross-sectional area (in$^2$) |
|---|---|---|---|
| 1 | 36.00 | 0.721 | 1.00 |
| 2 | 25.00 | 0.941 | 1.44 |
| 3 | 16.00 | 1.45 | 2.25 |
| 4 | 7.50 | 2.17 | 4.80 |
| 5 | 5.00 | 3.02 | 7.20 |
| 6 | 4.00 | 3.27 | 9.00 |
| 7 | 3.50 | 3.58 | 10.29 |
| 8 | 2.00 | 4.69 | 18.02 |
| 9 | 0.89 | 7.78 | 40.64 |
| 10 | 0.50 | 8.68 | 72.25 |

The data reveal that L/A ratios of 25 and greater reduce the UV radiation leakage to an amount that is below the 1 mW/m$^2$ exposure limit.

For example, computer-generated models tracing reflectance of UV radiation rays in three-dimensional space within the tested sanitizing chamber no. 2 (i.e., with L/A ratio of 25), no. 4 (i.e., with L/A ratio of 7.5), no. 6 (i.e., with L/A ratio of 4), and no. 9 (i.e., with L/A ratio of 0.89) are respectively shown in FIGS. 7A-7D. FIGS. 7E and 7F are irradiation maps that respectively show the amount of incident UV radiation escaping the sanitizing chambers modeled in FIGS. 7A and 7D. Specifically, the irradiation maps in FIGS. 7E and 7F provide the computer-modeled density of UV radiation rays measured at a cross-section near the exit end 702 of the particular sanitizing chamber.

Figure 7B:
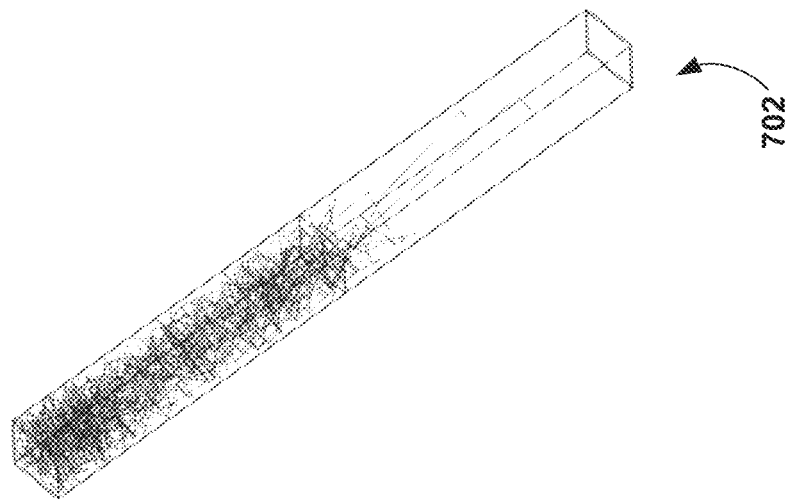
FIGS. 7A-7D are computer-generated three-dimensional representations of the reflectance of UV radiation within sanitizing chambers having various length-to-area ratios.
Figure 7A:
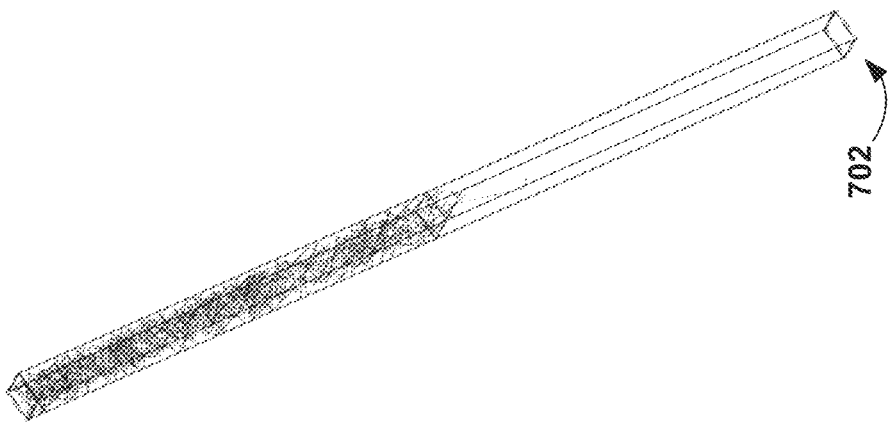
Figure 7D:
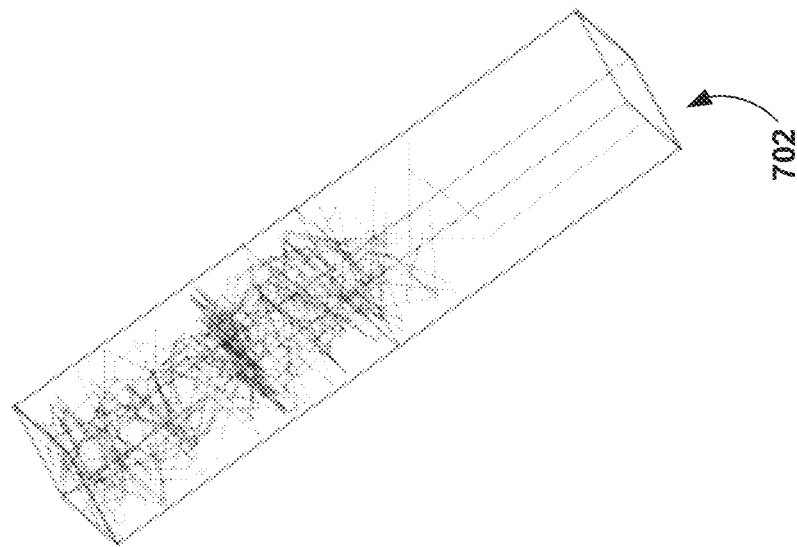
Figure 7C:
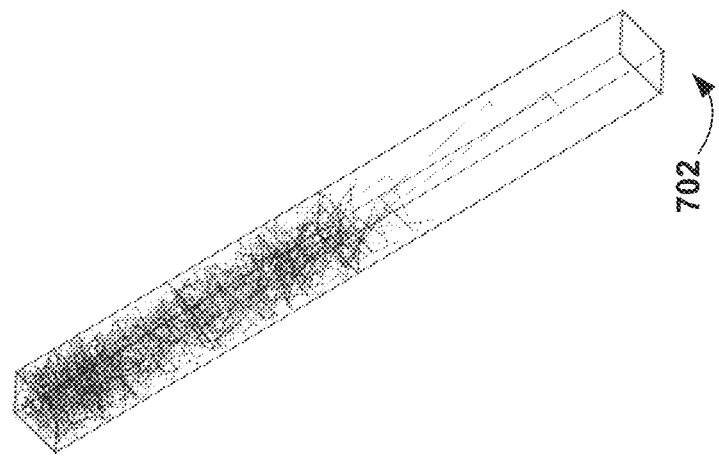
Figure 7F:
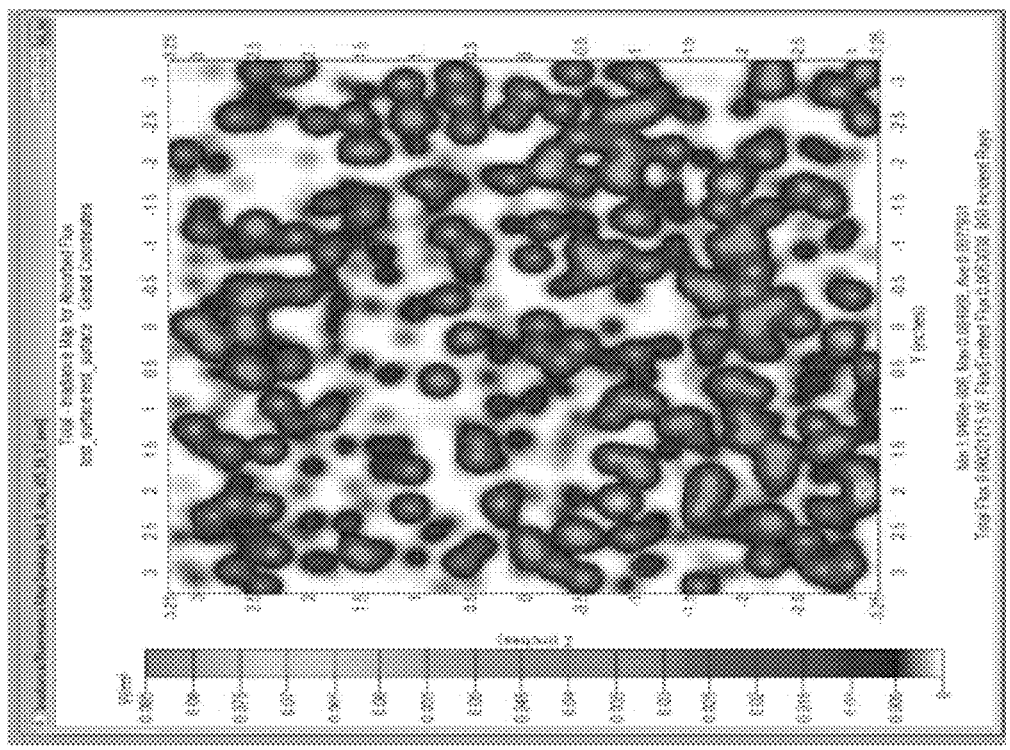
FIGS. 7E and 7F are computer-generated irradiation maps showing the amount of incident UV radiation escape from the sanitizing chambers represented in FIGS. 7A and 7B, respectively.
Figure 7E:
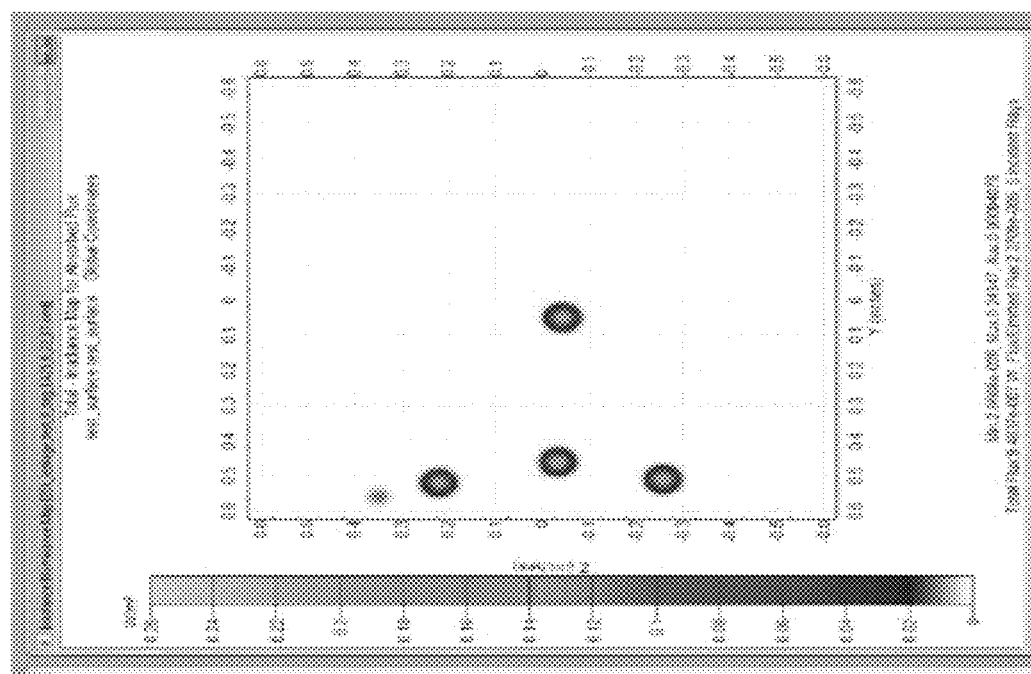

A visual comparison of FIGS. 7E and 7F demonstrates a far lower level of UV radiation escape occurring in FIG. 7E, which corresponds to the model of the sanitizing chamber having the L/A ratio of 25 (i.e., tested sanitizing chamber no. 2) shown in FIG. 7A.

Figure 8:
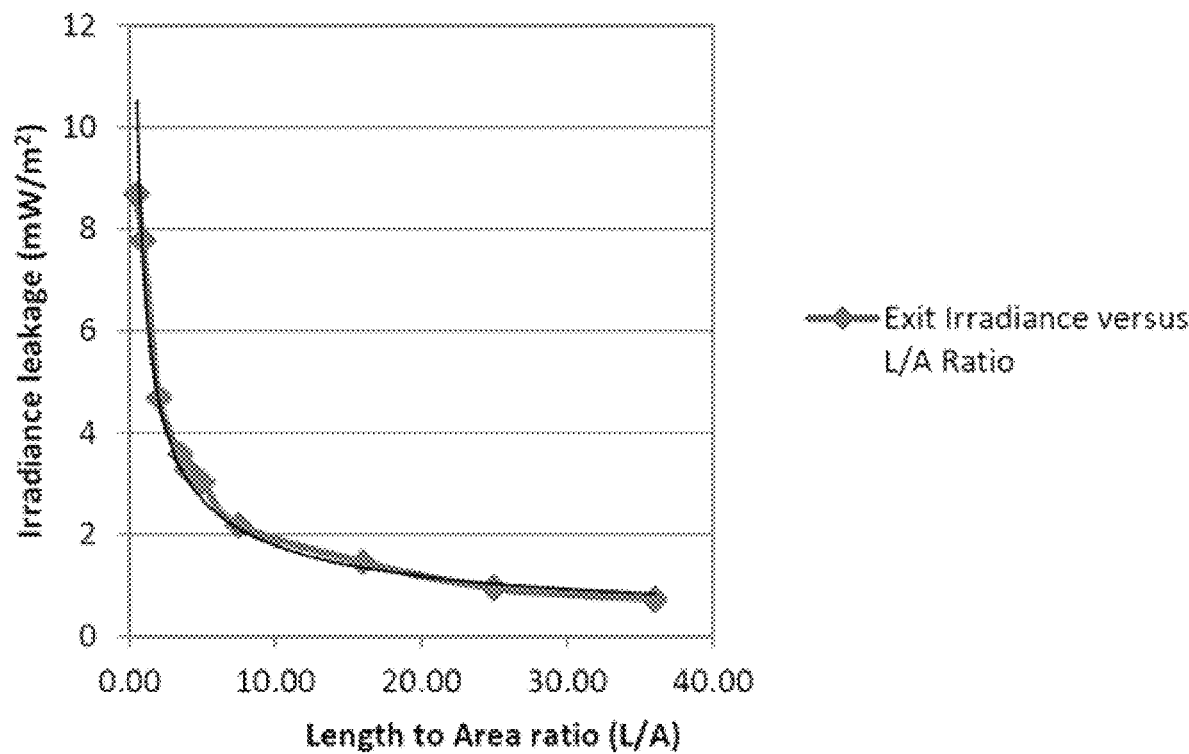
FIG. 8 is a graph illustrating the average UV radiation leakage measured as a function of the ratio of length to cross-sectional area for example sanitizing chambers.

FIG. 8 shows the average UV irradiance leakage for each of the sanitizing chambers 1-10 of Example 2. The data in the graph of FIG. 8 show a trend in which an increase in the L/A ratio reduces the average level of UV irradiance leakage measurement. Using an automatic curve fitting analysis, the following mathematical function was generated to represent the data points:

$$\text{Average UV radiation leakage} = 6.9656 \, (L/A \text{ ratio})^{-0.594} \quad \text{(Equation 1)}.$$

Together, the effective configurations for the sanitizing chamber that are shown above (i.e., bend angle of at least 90 degrees, and an L/A ratio of at least 25) may be implemented in combination and adjusted to identify optimal configurations for the particular sanitizing chamber properties (e.g., length of sanitizing chamber, number of bends, etc.).

The embodiments described above may be implemented in any of a variety of telephone types, including, but not limited to, devices and systems for residential use. The foregoing method descriptions are provided merely as illustrative examples and are not intended to require or imply that the processes of the various embodiments must be performed in the order presented. Skilled artisans may implement the described functionality in varying ways for each particular air treatment device, but such implementation decisions should not be interpreted as causing a departure from the scope of the present invention. Words such as "thereafter," "then," "next," etc. are not intended to limit the order of the processes; these words are simply used to guide the reader through the description of the methods. Further, any reference to claim elements in the singular, for example, using the articles "a," "an" or "the" is not to be construed as limiting the element to the singular.

The foregoing description of the various embodiments is provided to enable any person skilled in the art to make or use the present invention. Various modifications to these embodiments will be readily apparent to those skilled in the art, and the generic principles defined herein may be applied to other embodiments without departing from the scope of the invention. Thus, the present invention is not intended to be limited to the embodiments shown herein, and instead the claims should be accorded the widest scope consistent with the principles and novel features disclosed herein.

What is claimed is:

1. An air treatment system comprising:
   an air intake area comprising an opening and a filter assembly;
   a fan coupled to a sanitizing chamber, wherein the fan is configured to generate an airflow of filtered air through the sanitizing chamber; and
   an exhaust portion configured to release airflow that has passed through the sanitizing chamber, wherein the sanitizing chamber comprises:
     at least one bend having a total bend angle of at least 90 degrees; and
     at least one straight channel, wherein the at least one straight channel includes a sterilization region comprising an array of ultraviolet (UV) light emitting diodes (LEDs) configured to irradiate the airflow with UV radiation,
     wherein a ratio of a total length of the at least one straight channel of the sanitizing chamber to a cross-sectional area of the sanitizing chamber is at least 25.

2. The air treatment system of claim 1, wherein the at least one bend comprises a plurality of bends.

3. The air treatment system of claim 1, wherein the at least one bend has a total bend angle of at least 180 degrees.

4. The air treatment system of claim 1, wherein a length of the sterilization region is configured to minimize pressure drop across the air treatment system while enabling a 95% reduction of airborne pathogens from the airflow.

5. The air treatment system of claim 1, wherein the number of bends, the total bend angle, and the ratio of the total length of the sanitizing chamber to the cross-sectional area are configured to minimize pressure drop across the air treatment system while preventing escape of at least 93% of the UV radiation from the sanitizing chamber.

6. The air treatment system of claim 1, wherein the filter assembly comprises a pre-filter and one or more filter, wherein the filter assembly is configured to trap non-biological airborne contaminants.

7. The air treatment system of claim 6, wherein the one or more filter includes a high-efficiency particulate air (HEPA) filter.

8. The air treatment system of claim 1, wherein the array of UV LEDs is configured to emit radiation at one or more wavelength within a range of 240-280 nm.

9. The air treatment system of claim 1, wherein the UV LEDs are configured to irradiate the airflow with a UV radiation dosage, wherein the UV radiation dosage is calculated based on a computed residence time for the sanitizing chamber, computed UV radiation flux, and desired threshold of 95% reduction in airborne pathogens.

10. The air treatment system of claim 1, wherein the exhaust portion connects to a diffusion region of the sanitizing chamber, wherein the diffusion region is configured to prevent escape of UV radiation from the sanitizing chamber.

11. The air treatment system of claim 10, wherein a cross-sectional area of the diffusion region is graduated and has a largest value adjacent the exhaust portion.

12. The air treatment system of claim 1, wherein a UV-reflective material covers at least some of an interior surface of the sanitizing chamber.

13. The air treatment system of claim 1, wherein the at least one bend of the sanitizing chamber comprises:
   two bends adjacent opposite ends of the at least one straight channel;
   one or more bend in the diffusion region, wherein the one or more bend in the diffusion region has a smaller radius of curvature than the two bends adjacent opposite ends of the at least one straight channel.

14. The air treatment system of claim 1, further comprising a UV sensor disposed in the sanitizing chamber, and at least one visible indicator, wherein the UV sensor monitors performance of the array of UV LEDs, and the at least one visible indicator provides information to a user about the performance of the array of UV LEDs.

15. The air treatment system of claim 1, wherein the at least one straight channel comprises more than one straight channel.

16. A method of reducing airborne contaminants, the method comprising:
   filtering an airflow from a room to remove non-biological contaminants;
   generating an airflow that pushes filtered air to a contained ultraviolet (UV) radiation area;
   exposing the airflow in the contained UV radiation area to a predetermined UV radiation dosage; and
   exhausting the irradiated airflow from the contained UV radiation area back into the room, wherein:
     the contained UV radiation area comprises at least one bend having a total bend angle of at least 90 degrees and at least one straight channel; and a ratio of a total length of the at least one straight
channel of the contained UV radiation area to a
cross-sectional area of the contained UV radiation
area is at least 25.

\* \* \* \* \*